US00PP10679P

United States Patent [19]

Akerboom

[11] Patent Number: Plant 10,679

[45] Date of Patent: Nov. 10, 1998

[54] ASTER PLANT NAMED 'PARADE'

[75] Inventor: Petrus J. Akerboom, Ter Aar, Netherlands

[73] Assignee: De Nachtvlinder B.V., Ter Aar, Netherlands

[21] Appl. No.: 664,669

[22] Filed: Jun. 17, 1996

[51] Int. Cl.[6] ..... A01H 5/00

[52] U.S. Cl. ..... Plt./68.1

[58] Field of Search ..... Plt./68.1

[56] References Cited

PUBLICATIONS

The New Royal Horticultural Society Dictionary of Gardening; The Royal Horticultural Society; vol. 1; 1992; pp. 266–269.

UPOVROM Disk 1996 Mar. Search Results 3 pages.

*Primary Examiner*—Howard J. Locker
*Assistant Examiner*—Kent L. Bell
*Attorney, Agent, or Firm*—Foley & Lardner

[57] ABSTRACT

The new aster cultivar 'Parade' produces medium-sized flower heads with many medium length ray florets which have a distinctive purple color; an involucre that is long and funnel-shaped; and elliptic-shaped leaves that are medium-green in color and do not contain anthocyanin.

2 Drawing Sheets

The present invention comprises a new and distinct cultivar of aster plant hereinafter referred to by the cultivar name 'Parade'.

The new cultivar was originated from a cross made by the inventor in a controlled breeding program in Ter Aar, The Netherlands. The female or seed parent was a selection from proprietary breeding stock designed the "Butterfly family" while the male or pollen parent was a selection from proprietary breeding stock designated the "P" family. 'Parade' was discovered and selected by the inventor as a flowering plant within the progeny of the stated cross in a controlled environment in Ter Aar, The Netherlands. Asexual reproduction of the new cultivar, by cuttings, first performed in April 1993 by the inventor in Ter Aar, The Netherlands, and continuing thereafter, has demonstrated that the combination of characteristics as herein disclosed for the new cultivar are firmly fixed and retained through successive generations of asexual reproduction.

'Parade' has not been observed under all possible environmental conditions. The phenotype may vary with variations in environment such as temperature, light intensity and day length, without a change in the genotype of the plant. The following observations, measurements and values describe the new cultivar as grown in Bet Dagan, Israel, under conditions which closely approximate those generally used in commercial practice.

The following traits have been repeatedly observed and are determined to be basic characteristics of 'Parade' which in combination distinguish this aster as a new and distinct cultivar:

1. 'Parade' is of medium height at the time flowering commences.
2. 'Parade' produces relatively short elliptic shaped leaves of medium green color that do not contain anthocyanin coloration.
3. The first flower heads produced are located only at the distal parts.
4. The flower head is medium in size with many ray florets.
5. The ray florets are medium in length, narrowly elliptic, and purple in color (R.H.S. 87A) during winter flowering.
6. The involucre is long and funnel-shaped.
7. 'Parade' commences flowering very late compared to other asters.

The new cultivar is most similar to 'Milka' (U.S. plant patent application Ser. No. 08/664,519) and 'Karmijn' (U.S. plant patent application Ser. No. 08/664,520), both of which are described in co-pending applications of the inventor. These cultivars are similar because they each produce many ray florets and have a similar type of flower head. These cultivars differ, however, with respect to flower color, plant height, leaf color and leaf length.

The following Table provides several phenotypic characteristics that can be used to distinguish the aster varieties 'Parade', 'Milka' and 'Karmijn'.

| | Ray Florets | | | Capitulum | |
|---|---|---|---|---|---|
| | Colors (RHS) | Length (mm) | Diameter (mm) | Diameter (mm) | Involucre Shape |
| 'Parade' | Purple (87A) | 11–13 | 1.8 | 28–30 | Funnel-shaped, Long |
| 'Milka' | Violet (85A) | 14–16 | 2.0 | 24–27 | Cylindrical, Very Long |
| 'Karmijn' | Purple-Violet (81B) | 12–15 | 2.0 | 26–29 | Campanulate, Medium Length |

The accompanying photographs show a typical specimen plant of the new cultivar. The colors in the photographs are as true as possible with color illustrations of this type.

Sheet 1 is a side view of 'Parade'.

Sheet 2 is a close-up of a flower from the new variety.

In the following description, color references are made to The Royal Horticultural Society Colour Chart (R.H.S.), except where general colors of ordinary significance are referred to. Color values were taken indoors in a north light in Bet Dagan.

Botanical classification:

*Species name.*—Aster Novi-Belgii L.

*Cultivar name.*—'Parade'.

Parentage:

*Male parent.*—Proprietary selection from the P family.

*Female parent.*—Proprietary selection from the Butterfly family.

Propagation: The new cultivar holds its distinguishing characteristics through successive propagations by cuttings.

Inflorescence

A. Capitulum:
*Form.*—Convex.
*Type.*—Double.
*Diameter across face.*—28–30 mm.

B. Corolla of ray florets:
*Color* (*general tonality from a distance of three meters*).—Purple.
*Color* (*upper surface*).—Purple R.H.S. 87A.
*Color* (*under surface*).—Same as upper surface.
*Color* (*immature ray floret*).—Yellow.
*Shape.*—Narrow elliptic, acute apex.
*Size.*—11–13 mm in length×1.8 mm in width.
*Number of ray florets.*—124–163 per flower.

C. Corolla of disc florets: 'Parade' does not produce disc florets.

D. Reproductive organs:
*Androecium.*—Absent.
*Gynoecium.*—Present.

E. Buds:
*Size.*—8 mm diameter just before opening.
*Color.*—R.H.S. color of flower petals as the bud opens is 87A.

Plant

A. General appearance: The height of 'Parade' is medium, depending on light; but under continuous (up to 13½ hours) long day-length conditions, plant height can reach 2 m; branching is medium dense and there are few if any hairs on main stem.

B. Foliage:
*Color.*—Dark green, R.H.S. 137A.
*Shape.*—Elliptic.
*Margin.*—Dentations on whole margin.
*Size.*—The first internode is at the first side flower under the top flower. Length: 5th Internode: 25–37 mm. 10th Internode: 33–58 mm. 15th Internode: 70–80 mm. 20th Internode: 84–106 mm. Width: 5th Internode: 3.0–3.8 mm. 10th Internode: 4.0–5.5 mm. 15th Internode: 6.5–7.0 mm. 20th Internode: 9.0–10.5 mm.

C. Stem:
*Length of internode.*—5th Internode: 10–14 mm. 10th Internode: 13–19 mm. 15th Internode: 15–26 mm. 20th Internode: 18–25 mm.
*Thickness of Internodes.*—5th Internode: 1.0–2.0 mm. 10th Internode: 1.3–2.0 mm. 15th Internode: 2.2–3.0 mm. 20th Internode: 3.0–3.5 mm.

D. Side branch:
*Length of Internode.*—5th Internode: 21–36 mm. 10th Internode: 33–50 mm. 15th Internode: 49–105 mm. 20th Internode: 80–158 mm.

E. Disease resistance: No abnormal disease problems have been noted to date. Accordingly, the disease resistance exhibited by this cultivar when compared to other known commercial aster varieties is not unique. However, the cultivar does appear to exhibit some resistance to tomato spotted wilt virus.

F. Fertility: Does not produce pollen and therefore is male sterile but can serve as a female parent in crosses.

I claim:

1. A new and distinct cultivar of aster plant named 'Parade', as illustrated and described.

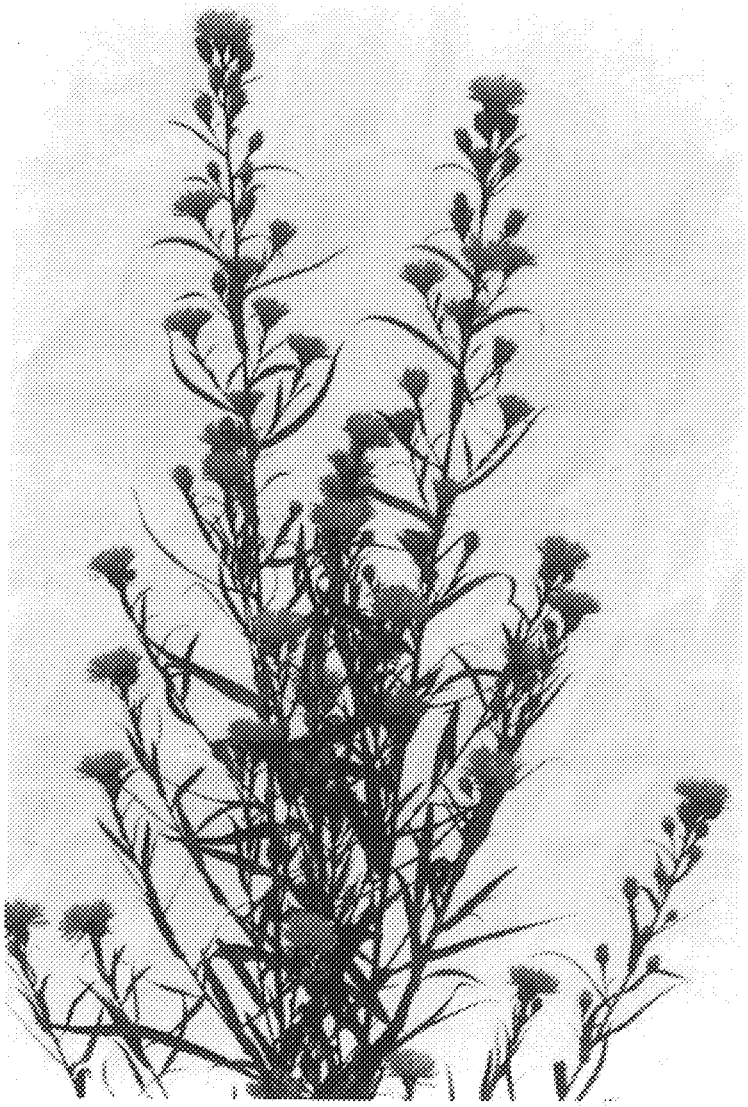

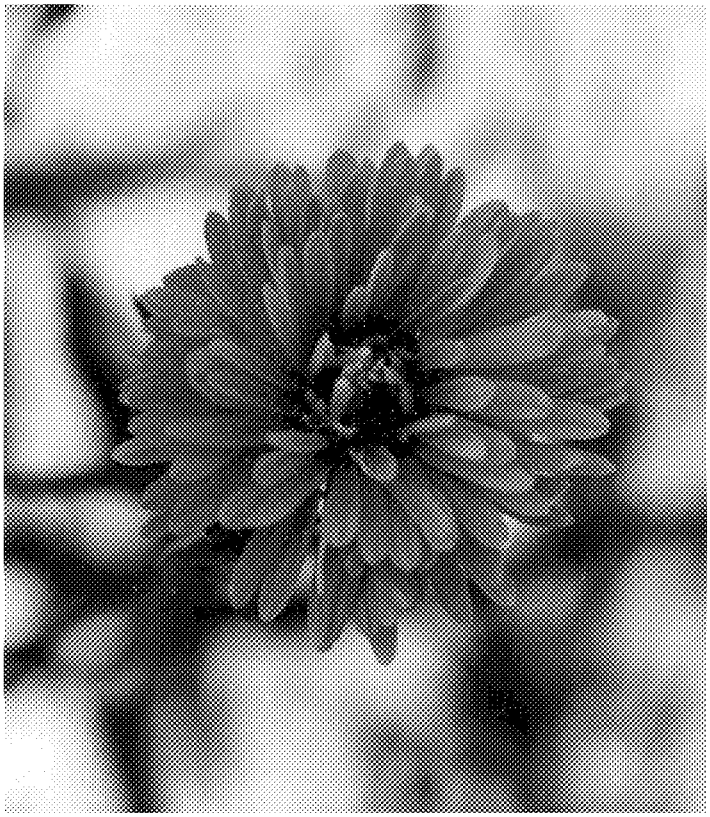

* * * * *